US010395510B2

(12) United States Patent
Du et al.

(10) Patent No.: US 10,395,510 B2
(45) Date of Patent: Aug. 27, 2019

(54) REMINDING METHOD AND REMINDING DEVICE

(71) Applicant: Beijing Zhigu Rui Tuo Tech Co., Ltd, Beijing (CN)

(72) Inventors: Lin Du, Beijing (CN); Hongjiang Zhang, Beijing (CN)

(73) Assignee: BEIJING ZHIGU RUI TUO TECH CO., LTD, Beijing (CN)

(*) Notice: Subject to any disclaimer, the term of this patent is extended or adjusted under 35 U.S.C. 154(b) by 0 days.

(21) Appl. No.: 14/783,495

(22) PCT Filed: Dec. 4, 2013

(86) PCT No.: PCT/CN2013/088549
§ 371 (c)(1),
(2) Date: Oct. 9, 2015

(87) PCT Pub. No.: WO2015/027598
PCT Pub. Date: Mar. 5, 2015

(65) Prior Publication Data
US 2016/0180692 A1 Jun. 23, 2016

(30) Foreign Application Priority Data
Aug. 30, 2013 (CN) .......................... 2013 1 0390569

(51) Int. Cl.
G08B 23/00 (2006.01)
G08B 21/24 (2006.01)
(Continued)

(52) U.S. Cl.
CPC ............ *G08B 21/24* (2013.01); *A61B 3/0025* (2013.01); *A61B 3/12* (2013.01); *A61B 3/14* (2013.01);
(Continued)

(58) Field of Classification Search
CPC . A61L 35/18; G06F 3/013; G02B 2027/0127; G02B 2027/0138;
(Continued)

(56) References Cited

U.S. PATENT DOCUMENTS 4,264,154 A 4/1981 Petersen
4,572,616 A 2/1986 Kowel et al.
(Continued)

FOREIGN PATENT DOCUMENTS

CN 1372650 10/2002
CN 1470227 1/2004
(Continued)

OTHER PUBLICATIONS

International Search Report dated Jun. 5, 2014 for PCT Application No. PCT/CN2013/088549, 4 pages.
(Continued)

Primary Examiner — Naomi J Small
(74) Attorney, Agent, or Firm — Amin, Turocy & Watson, LLP

(57) ABSTRACT

Disclosed are an alert method and apparatus, and the present application relates to the field of intelligent alert technologies. The method comprising: detecting a focusing point position of a sightline of a user; and alerting the user according to the focusing point position and a state of the user. For the method and apparatus in the embodiments of the present application, a focusing point position of a sightline of a user can be detected precisely, and the user can be alerted accurately according to the focusing point position, so that the application range of the method and apparatus is relatively wide. In addition, according to a state of a user, user data, and the like, a monitoring parameter is selected and an alert threshold is set, so that the user can be properly alerted in a more targeted manner.

28 Claims, 7 Drawing Sheets

(51) Int. Cl.

| | | |
|---|---|---|
| *A61B 5/18* | (2006.01) | |
| *G06F 3/01* | (2006.01) | |
| *G02B 27/00* | (2006.01) | |
| *A61B 5/00* | (2006.01) | |
| *G02B 27/01* | (2006.01) | |
| *A61B 3/00* | (2006.01) | |
| *A61B 3/12* | (2006.01) | |
| *A61B 3/14* | (2006.01) | |
| *A61B 3/113* | (2006.01) | |

(52) U.S. Cl.
CPC .............. *A61B 5/18* (2013.01); *A61B 5/6803* (2013.01); *G02B 27/0093* (2013.01); *G02B 27/017* (2013.01); *G06F 3/013* (2013.01); *A61B 3/113* (2013.01); *G02B 2027/014* (2013.01); *G02B 2027/0127* (2013.01); *G02B 2027/0138* (2013.01); *G02B 2027/0178* (2013.01)

(58) Field of Classification Search
CPC ...... G02B 2027/014; G02B 2027/0178; G02B 27/0093; G02B 27/017; G08B 21/24; A61B 3/113; A61B 3/12; A61B 3/14; A61B 3/0025; A61B 5/18; A61B 5/6803
USPC ........................................................ 340/573.1
See application file for complete search history.

(56) References Cited

U.S. PATENT DOCUMENTS

| | | | |
|---|---|---|---|
| 4,973,149 | A | 11/1990 | Hutchinson |
| 5,182,585 | A | 1/1993 | Stoner |
| 5,537,163 | A | 7/1996 | Ueno |
| 6,072,443 | A | 6/2000 | Nasserbakht et al. |
| 6,111,597 | A | 8/2000 | Tabata |
| 6,151,061 | A | 11/2000 | Tokuhashi |
| 6,152,563 | A | 11/2000 | Hutchison et al. |
| 6,325,513 | B1 | 12/2001 | Bergner et al. |
| 7,001,020 | B2 | 2/2006 | Yancey et al. |
| 7,298,414 | B2 | 11/2007 | Stavely et al. |
| 7,334,892 | B2 | 2/2008 | Goodall et al. |
| 7,486,988 | B2 | 2/2009 | Goodall et al. |
| 7,764,433 | B2 | 7/2010 | Kam et al. |
| 7,766,479 | B2 | 8/2010 | Ebisawa |
| 8,104,892 | B2 | 1/2012 | Hillis et al. |
| 8,109,632 | B2 | 2/2012 | Hillis et al. |
| 8,282,212 | B2 | 10/2012 | Hillis et al. |
| 8,384,999 | B1 | 2/2013 | Crosby et al. |
| 8,896,632 | B2 | 11/2014 | MacDougall et al. |
| 2002/0101568 | A1 | 8/2002 | Eberl et al. |
| 2002/0113943 | A1 | 8/2002 | Trajkovic et al. |
| 2003/0043303 | A1 | 3/2003 | Karuta et al. |
| 2003/0125638 | A1 | 7/2003 | Husar et al. |
| 2005/0003043 | A1 | 1/2005 | Sewal et al. |
| 2005/0014092 | A1 | 1/2005 | Hasegawa et al. |
| 2005/0030438 | A1 | 2/2005 | Nishioka |
| 2006/0016459 | A1 | 1/2006 | Mcfarlane et al. |
| 2006/0103808 | A1* | 5/2006 | Horie ...................... A61H 5/00 351/202 |
| 2006/0122530 | A1 | 6/2006 | Goodall et al. |
| 2006/0146281 | A1 | 7/2006 | Goodall et al. |
| 2006/0164593 | A1 | 7/2006 | Peyghambarian et al. |
| 2006/0122531 | A1 | 8/2006 | Goodall et al. |
| 2007/0019157 | A1 | 1/2007 | Hills et al. |
| 2007/0211207 | A1 | 9/2007 | Lo et al. |
| 2008/0002262 | A1 | 1/2008 | Chirieleison |
| 2008/0106633 | A1 | 5/2008 | Blum et al. |
| 2009/0066915 | A1 | 3/2009 | Lai |
| 2009/0189974 | A1 | 7/2009 | Deering |
| 2009/0279046 | A1 | 11/2009 | Dreher et al. |
| 2009/0303212 | A1 | 12/2009 | Akutsu et al. |
| 2010/0053539 | A1 | 3/2010 | Lin |
| 2011/0018903 | A1 | 1/2011 | Lapstun et al. |
| 2011/0019258 | A1 | 1/2011 | Levola |
| 2011/0213462 | A1 | 1/2011 | Holladay |
| 2011/0051087 | A1 | 3/2011 | Inoue et al. |
| 2011/0199202 | A1* | 8/2011 | De Mers ................ A61B 5/18 340/439 |
| 2011/0242277 | A1 | 10/2011 | Do et al. |
| 2011/0279277 | A1 | 11/2011 | Li-Chung |
| 2012/0007959 | A1 | 1/2012 | Kwon et al. |
| 2012/0013389 | A1 | 1/2012 | Thomas et al. |
| 2012/0038549 | A1 | 2/2012 | Mandella et al. |
| 2012/0092618 | A1 | 4/2012 | Yoo et al. |
| 2012/0113235 | A1* | 5/2012 | Shintani .............. H04N 13/337 348/51 |
| 2012/0127062 | A1 | 5/2012 | Bar-Zeev et al. |
| 2012/0127422 | A1 | 5/2012 | Tian et al. |
| 2012/0133891 | A1 | 5/2012 | Jiang |
| 2012/0140044 | A1 | 6/2012 | Galstian et al. |
| 2012/0154277 | A1* | 6/2012 | Bar-Zeev ............. G02B 27/017 345/158 |
| 2012/0169730 | A1 | 7/2012 | Inoue |
| 2012/0206485 | A1 | 8/2012 | Osterhout et al. |
| 2012/0212499 | A1 | 8/2012 | Haddick et al. |
| 2012/0212508 | A1 | 8/2012 | Kimball |
| 2012/0242698 | A1 | 9/2012 | Haddick et al. |
| 2012/0290401 | A1 | 11/2012 | Neven |
| 2012/0293773 | A1 | 11/2012 | Publicover et al. |
| 2012/0307208 | A1 | 12/2012 | Trousdale |
| 2013/0044042 | A1 | 2/2013 | Olsson et al. |
| 2013/0050432 | A1* | 2/2013 | Perez ................... G02B 27/017 348/47 |
| 2013/0050646 | A1 | 2/2013 | Nanbara |
| 2013/0072828 | A1 | 3/2013 | Sweis et al. |
| 2013/0093997 | A1 | 4/2013 | Utsunomiya et al. |
| 2013/0107066 | A1 | 5/2013 | Venkatraman et al. |
| 2013/0127980 | A1 | 5/2013 | Haddick et al. |
| 2013/0135203 | A1 | 5/2013 | Croughwell, III |
| 2013/0147836 | A1 | 6/2013 | Small et al. |
| 2013/0194323 | A1 | 8/2013 | Choi et al. |
| 2013/0215504 | A1 | 8/2013 | Kim et al. |
| 2013/0241805 | A1* | 9/2013 | Gomez ................... G09G 3/003 345/8 |
| 2013/0241927 | A1 | 9/2013 | Vardi |
| 2013/0278631 | A1 | 10/2013 | Border et al. |
| 2013/0335301 | A1 | 12/2013 | Wong et al. |
| 2013/0335404 | A1 | 12/2013 | Westerinen et al. |
| 2013/0335833 | A1 | 12/2013 | Liao et al. |
| 2013/0342572 | A1 | 12/2013 | Poulos et al. |
| 2014/0078175 | A1* | 3/2014 | Forutanpour ........ G02B 27/017 345/633 |
| 2014/0160157 | A1 | 6/2014 | Poulos et al. |
| 2014/0225915 | A1 | 8/2014 | Theimer et al. |
| 2014/0225918 | A1 | 8/2014 | Mittal et al. |
| 2014/0232746 | A1 | 8/2014 | Ro et al. |
| 2014/0240351 | A1 | 8/2014 | Scavezze et al. |
| 2014/0267400 | A1 | 9/2014 | Mabbutt et al. |
| 2014/0267420 | A1 | 9/2014 | Schowengerdt et al. |
| 2014/0282224 | A1 | 9/2014 | Pedley |
| 2014/0327875 | A1 | 11/2014 | Blum et al. |
| 2014/0354514 | A1* | 12/2014 | Aronsson ................ G06F 3/013 345/7 |
| 2014/0375680 | A1 | 12/2014 | Ackerman et al. |
| 2015/0002542 | A1 | 1/2015 | Chan et al. |
| 2015/0035861 | A1 | 2/2015 | Salter et al. |
| 2015/0234184 | A1 | 8/2015 | Schowengerdt et al. |
| 2015/0235427 | A1 | 8/2015 | Nobori et al. |
| 2015/0235632 | A1 | 8/2015 | Liu et al. |
| 2015/0070391 | A1 | 9/2015 | Nishimaki et al. |
| 2016/0034032 | A1 | 2/2016 | Jeong |
| 2016/0035139 | A1 | 2/2016 | Fuchs et al. |
| 2016/0062454 | A1 | 3/2016 | Wang et al. |
| 2016/0171772 | A1 | 6/2016 | Ryznar et al. |
| 2016/0189432 | A1 | 6/2016 | Bar-Zeev et al. |
| 2016/0196603 | A1 | 7/2016 | Perez et al. |
| 2016/0299360 | A1 | 10/2016 | Fonte et al. |

(56) References Cited

U.S. PATENT DOCUMENTS

| | | |
|---|---|---|
| 2016/0370605 A1 | 12/2016 | Ain-Kedem |
| 2017/0092235 A1 | 3/2017 | Osman et al. |

FOREIGN PATENT DOCUMENTS

| | | |
|---|---|---|
| CN | 1141602 | 3/2004 |
| CN | 1527126 | 9/2004 |
| CN | 1604014 | 4/2005 |
| CN | 1645244 | 7/2005 |
| CN | 1653374 | 8/2005 |
| CN | 1901833 | 1/2007 |
| CN | 1912672 | 2/2007 |
| CN | 2868183 | 2/2007 |
| CN | 1951314 | 4/2007 |
| CN | 101069106 | 11/2007 |
| CN | 101072534 | 11/2007 |
| CN | 101097293 | 1/2008 |
| CN | 101103902 | 1/2008 |
| CN | 201005945 | 1/2008 |
| CN | 101116609 | 2/2008 |
| CN | 101155258 | 4/2008 |
| CN | 101194198 | 6/2008 |
| CN | 101430429 | 5/2009 |
| CN | 201360319 | 9/2009 |
| CN | 201352278 | 11/2009 |
| CN | 101900927 | 1/2010 |
| CN | 101662696 | 3/2010 |
| CN | 201464738 | 5/2010 |
| CN | 101782685 | 7/2010 |
| CN | 101819331 | 9/2010 |
| CN | 101819334 | 9/2010 |
| CN | 201637953 | 11/2010 |
| CN | 101917638 | 12/2010 |
| CN | 201754203 | 3/2011 |
| CN | 102008288 A | 4/2011 |
| CN | 102083390 | 6/2011 |
| CN | 102203850 | 9/2011 |
| CN | 102292017 | 12/2011 |
| CN | 102419631 | 4/2012 |
| CN | 102481097 | 5/2012 |
| CN | 101149254 | 6/2012 |
| CN | 102487393 | 6/2012 |
| CN | 202267785 | 6/2012 |
| CN | 102572483 | 7/2012 |
| CN | 102576154 | 7/2012 |
| CN | 202383380 | 8/2012 |
| CN | 102918444 | 2/2013 |
| CN | 102939557 | 2/2013 |
| CN | 102981270 | 3/2013 |
| CN | 103054695 | 4/2013 |
| CN | 103065605 | 4/2013 |
| CN | 103150013 | 6/2013 |
| CN | 103190883 A | 7/2013 |
| CN | 103197757 | 7/2013 |
| CN | 103280175 | 9/2013 |
| CN | 103297735 | 9/2013 |
| CN | 103353663 | 10/2013 |
| CN | 103353667 | 10/2013 |
| CN | 103353677 | 10/2013 |
| CN | 103558909 | 2/2014 |
| DE | 19959379 | 7/2000 |
| EP | 2646859 | 10/2013 |
| JP | 03023431 | 1/1991 |
| JP | 2676870 | 11/1997 |
| JP | H09289973 A | 11/1997 |
| JP | 3383228 | 3/2003 |
| JP | 2003307466 | 10/2003 |
| JP | 2005058399 | 3/2005 |
| JP | 2007129587 | 5/2007 |
| JP | 201143876 | 3/2011 |
| JP | 2012199621 | 10/2012 |
| JP | 2012247449 | 12/2012 |
| TW | 201012448 | 4/2010 |
| WO | 2004023167 | 3/2004 |
| WO | 2005077258 A1 | 8/2005 |
| WO | 2012075218 | 6/2012 |
| WO | 2012083415 | 6/2012 |
| WO | 2013074851 | 5/2013 |

OTHER PUBLICATIONS

Smith, et al. "Determining Driver Visual Attention With One Camera", IEEE Transactions on Intelligent Transportation Systems, vol. 4, No. 4, Dec. 2003, 14 pages.

Singh, et al. "Human Eye Tracking and Related Issues: A Review", International Journal of Scientific and Research Publications, vol. 2, Issue 9, Sep. 2012, ISSN 2250-3153, 9 pages.

Ji, et al. "Real-Time Eye, Gaze, and Face Pose Tracking for Monitoring Driver Vigilance", Real-Time Imaging 8, 357-377 (2002), available online at http://www.idealibrary.com, 21 pages.

Office Action dated May 3, 2017 for U.S. Appl. No. 14/781,306, 46 pages.

Office Action dated Mar. 30, 2017 for U.S. Appl. No. 15/028,019, 36 pages.

Office Action dated Apr. 21, 2017 for U.S. Appl. No. 14/781,581, 19 pages.

Office Action dated Apr. 20, 2017 for U.S. Appl. No. 14/781,578, 77 pages.

International Search Report dated Mar. 6, 2014 for PCT Application No. PCT/CN2013/088540, 8 pages.

Jeong, et al. "Tunable microdoublet lens array", Optics Express, vol. 12, Issue 11, May 2004, pp. 2494-2500.

International Search Report dated Apr. 3, 2014 for PCT Application No. PCT/CN2013/088531, 10 pages.

International Search Report dated Feb. 27, 2014 for PCT Application No. PCT/CN2013/088522, 6 pages.

International Search Report dated May 8, 2014 for PCT Application No. PCT/CN2013/088547, 4 pages.

Kim et al., "A 200 s Processing Time Smart Image Sensor for an Eye Tracker using pixel-level analog image processing", IEEE Journal of Solid-State Circuits, vol. 44, No. 9, Sep. 2009, 10 pages.

Hansen et al., "In the eye of the beholder: a survey of models for eyes and gaze", IEEE Transactions on pattern analysis and machine intelligence, vol. 32, No. 3, Mar. 2010, 23 pages.

International Search Report dated May 28, 2014 for PCT Application No. PCT/CN2013/088553, 6 pages.

International Search Report dated May 28, 2014 for PCT Application No. PCT/CN2013/088545, 4 pages.

Office Action dated Jun. 8, 2017 for U.S. Appl. No. 14/779,968, 79 pages.

Office Action dated Jun. 29, 2017 for U.S. Appl. No. 14/783,503, 120 pages.

Gao et al. "Measuring Directionality of the Retinal Reflection with a Shack-Hartmann Wavefront Sensor", Dec. 2009, Optics Express, vol. 17, No. 25, Optical Society of America, 20 pages.

Office Action dated Jul. 12, 2017 for U.S. Appl. No. 14/780,519, 45 pages.

Office Action dated Oct. 4, 2017 for U.S. Appl. No. 14/781,584, 95 pages.

Office Action dated Nov. 9, 2017 for U.S. Appl. No. 14/781,578, 64 pages.

Office Action dated Nov. 9, 2017 for U.S. Appl. No. 14/780,519, 24 pages.

Office Action dated Dec. 19, 2017 for U.S. Appl. No. 14/783,503, 78 pages.

Lee et al. "A Robust Eye Gaze Tracking Method Based on a Virtual Eyeball Model", Machine Vision and Applications, (2009) 20:319-337, Springer-Verlag, 2008. 19 pages.

Office Action dated Dec. 14, 2017 for U.S. Appl. No. 14/779,321, 82 pages.

Office Action dated Dec. 15, 2017 for U.S. Appl. No. 14/779,968, 67 pages.

Office Action dated Feb. 5, 2018 for U.S. Appl. No. 14/779,321, 38 pages.

International Search report dated Jun. 12, 2014 for PCT Application No. PCT/CN2013/088554, 4 pages.

(56) References Cited

OTHER PUBLICATIONS

International Search Report dated Jan. 8, 2015 for PCT Application No. PCT/CN2014/088242, 2 pages.
International Search Report dated May 5, 2014 for PCT Application No. PCT/CN2013/088544, 4 pages.
Office Action dated Dec. 29, 2016 for U.S. Appl. No. 14/780,519, 25 pages.
Office Action dated Jun. 29, 2018 for U.S. Appl. No. 14/781,578, 67 pages.
Office Action dated Jun. 25, 2018 for U.S. Appl. No. 14/779,321, 43 pages.
Office Action dated Jun. 14, 2018 for U.S. Appl. No. 14/780,519, 29 pages.
Notice of Allowance dated Sep. 11, 2018 for U.S. Appl. No. 14/780,519, 29 pages.
Office Action dated Jul. 17, 2018 for U.S. Appl. No. 14/781,584, 75 pages.
Office Action dated Sep. 20, 2018 for U.S. Appl. No. 14/779,968, 71 pages.
Notice of Allowance dated Nov. 20, 2018 for U.S. Appl. No. 14/779,321, 31 pages.
Office Action dated Feb. 4, 2019 for U.S. Appl. No. 14/781,578, 69 pages.

\* cited by examiner

REMINDING METHOD AND REMINDING DEVICE

RELATED APPLICATIONS

This application is a U.S. National Stage filing under 35 U.S.C. § 371 of international patent cooperation treaty (PCT) application No. PCT/CN2013/088549, filed Dec. 4, 2013, and entitled "REMINDING METHOD AND REMINDIGN DEVICE", which claims the priority of Chinese Patent Application No. 201310390569.9, filed with the Chinese Patent Office on Aug. 30, 2013 and entitled "ALERT METHOD AND APPARATUS", which applications are hereby incorporated herein by reference in their respective entireties.

TECHNICAL FIELD

The present application relates to the field of intelligent alert technologies, and in particular, to an alert method and apparatus.

BACKGROUND

According to researches, in addition to causes such as age and heredity, unhealthy and even incorrect use of eyes is the main cause of a vision decline. For example, eyes are used for a long time, at a short distance, and the like. Besides the vision decline, in some scenarios, incorrect use of eyes may result in extremely severe consequences. For example, in a driving state, if a driver fails to concentrate and gazes in an incorrect direction, a traffic accident may occur, causing a great threat to personal safety.

To protect vision and urge correct use of eyes, there is a method of measuring a distance from eyes to an object in front of a user and sending an alert when the distance is inappropriate. The method may have a desirable effect of reminding a user in a certain application scenario such as reading and writing. However, in the method, as a distance between eyes and an object in front is measured, and the object is not necessarily a position at which a user actually gazes, the application range of the method is limited and a false alert may be sent in a specific scenario.

SUMMARY

An example, non-limiting objective of the present application is to provide an alert method and apparatus, which can send an alert more accurately and have a wide application range.

To these and/or related ends, in a first embodiment an embodiment of the present application provides an alert method, wherein the method comprises:
  detecting a focusing point position of a sightline of a user; and
  alerting the user according to the focusing point position and a state of the user.

In a second embodiment, an embodiment of the present application provides an alert apparatus, wherein the apparatus comprising:
  a detection module, configured to detect a focusing point position of a sightline of a user; and
  an alert module, configured to alert the user according to the focusing point position and a state of the user.

In a third embodiment, an embodiment of the present application provides a computer program product, wherein the computer program product causes an alert apparatus to execute the method in the first aspect or in any possible implementation manner of the first aspect.

In a fourth embodiment, an embodiment of the present application provides a computer readable medium, wherein the computer readable medium comprises a computer operation instruction, and when being executed by a processor, the computer operation instruction is configured to cause the processor to execute the method in the first aspect or in any possible implementation manner of the first aspect.

In a fifth embodiment, an embodiment of the present application provides an alert apparatus comprising a processor, a memory, and a communications interface, wherein
  the memory stores a computer operation instruction, the processor, the memory, and the communications interface are connected through a communication bus, and
  when the apparatus is operated, the processor executes the computer operation instruction stored in the memory, which causes the apparatus to execute the method in the first aspect or in any possible implementation manner of the first aspect.

For the method and apparatus in the embodiments of the present application, a focusing point position of a sightline of a user can be detected precisely, and the user can be alerted accurately according to the focusing point position, so that the application range of the method and apparatus is relatively wide. In addition, according to a state of a user, user data, and the like, a monitoring parameter is selected and an alert threshold is set, so that the user can be properly alerted in a more targeted manner.

DETAILED DESCRIPTION

Specific implementation manners of the present application are further described in detail below with reference to the accompanying drawings and embodiments. The embodiments below are only used to describe the present application, but do not intend to limit the scope of the present application.

When a human eye is viewing a target object, the process in which the object is clearly imaged on a retina may be referred to as focusing of an eye, and correspondingly, the clearest imaging point on the retina is a focusing point of a sightline when the human eye is viewing the target object.

Figure 1:
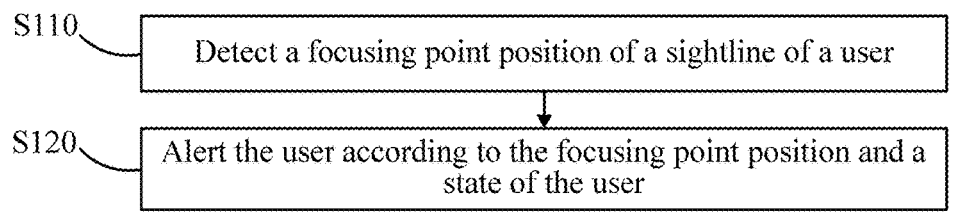
FIG. 1 is an example flowchart of an alert method according to an embodiment of the present application.

As shown in FIG. 1, an alert method is provided in an embodiment of the present application. The method comprises the following steps:

S110. Detect a focusing point position of a sightline of a user.

S120. Alert the user according to the focusing point position and a state of the user.

For the method of the embodiment of the present application, a focusing point position of a sightline of a user is detected, so as to send an alert more accurately based on an object at which a human eye gazes, so that the application range is relatively wide.

In the method of the embodiment of the present application, a focusing point position of a sightline of a user may be detected in multiple manners. For example:

a) A pupil direction detector is used to detect an eye optical axis direction, and then the depth of filed at which the eye gaze is obtained by using a depth sensor (for example, infrared distance measurement), so that a focusing point position of a sightline of the eye is obtained.

b) Optical axis directions of two eyes are separately detected, and an intersection point of the optical axis directions of the two eyes is obtained, so that a focusing point position of a sightline of an eye is obtained.

c) According to an optical parameter of an optical path between an image collecting position and an eye, when a clearest image presented on an imaging surface of the eye is collected, a focusing point position of a sightline of the eye of the user is obtained. Specifically, Step S110 may further comprise:

S111. Collect an image presented by a fundus of an eye of a user.

S112. Adjust an imaging parameter of an optical path between the eye of the user and a collecting position until a clearest image is collected.

S113. Process the collected image, and obtain the focusing point position through calculation according to the imaging parameter of the optical path between the eye of the user and the collecting position when the clearest image is collected and an optical parameter of the eye of the user, wherein the optical parameter of the eye of the user comprises an eye optical axis direction.

For the foregoing method, an image on a fundus of an eye of a user is analyzed and processed to obtain an optical parameter of the eye when a clearest image is collected, so as to obtain a current focusing point position of the eye of the user through calculation, thereby providing a basis for further alerting the user based on the precise focusing point position.

Herein, the image presented by the "fundus" mainly is an image presented on a retina, which may be an image of the fundus or an image, of another object, cast to the fundus.

In Step S112, by adjusting the focal length of an optical device in an optical path between an eye of a user and a collecting position, and/or adjusting a location of the optical device in the optical path, a clearest image of the fundus may be obtained when the optical device is at a certain position or in a certain state. The adjustment may be continuous and in real time.

In a possible implementation manner of the method of the embodiment of the present application, the optical device may be a focal length adjustable lens, configured to adjust the refractive index and/or the shape thereof to accomplish the adjustment of the focal length thereof. Specifically: 1) The focal length is adjusted by adjusting the curvature of at least one surface of the focal length adjustable lens; for example, the curvature of the focal length adjustable lens is adjusted by increasing or reducing the liquid medium in a cavity constructed by a double-layer transparent layer; and 2) The focal length is adjusted by changing the refractive index of the focal length adjustable lens; for example, the focal length adjustable lens is filled with a specific liquid crystal medium, and the arrangement manner of the liquid crystal medium is adjusted by adjusting a voltage of an electrode corresponding to the liquid crystal medium, so as to change the refractive index of the focal length adjustable lens.

In another implementation manner of the method of the embodiment of the present application, the optical device may be: a lens set, configured to accomplish the adjustment of the focal length of the lens group by adjusting relative positions between lenses of the lens set.

In addition to the foregoing two methods in which a parameter of an optical path is changed by means of features of the optical device, the parameter of an optical path may also be changed by adjusting the position of the optical device in the optical path.

In addition, in the method of the embodiment of the present application, Step S113 further comprises:

S1131. Analyze the image collected in Step S111 to find the clearest image.

S1132. Obtain the optical parameter of the eye of the user through calculation according to the clearest image and the imaging parameter known when the clearest image is obtained.

The adjustment in Step S112 makes it possible to collect the clearest image, but the clearest image needs to be found through Step S113, and the optical parameter of the eye of the user may be obtained through calculation according to the clearest image and the known parameter of the optical path.

Figure 2A:
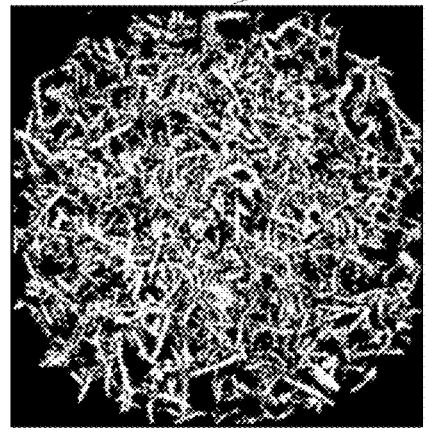
FIG. 2(a) is an example diagram of a light spot pattern.
Figure 2B:
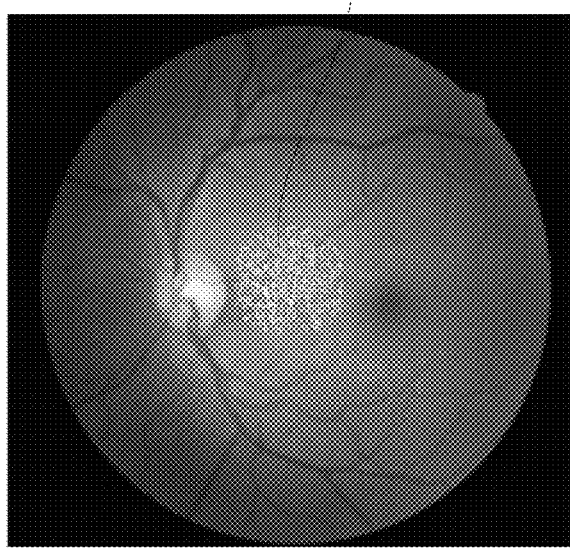
FIG. 2(b) is an image, of the fundus of a user, collected according to a method in an embodiment of the present application when a light spot pattern shown in FIG. 2(a) is cast.

In the method of the embodiment of the present application, Step S113 may further comprise:

S1133. Cast a light spot to the fundus of the user. The cast light spot may have no specific pattern and be only used to light up the fundus of the user. The cast light spot may further comprise a pattern rich in features. The pattern rich in features may facilitate detection, so as to improve the precision of detection. As shown in FIG. 2(a), FIG. 2(a) is an example diagram of a light spot pattern 200, and the pattern may be formed by a light spot pattern generator, for example, a frosted glass; FIG. 2(b) shows an image, of the fundus of a user, collected when the light spot pattern 200 is cast.

To avoid affecting normal viewing of the eye, preferably, the light spot is an infrared light spot invisible to the eye. In this case, to reduce interferences from other spectrums: steps for filtering out lights, in the cast light spot, other than the invisible light transmitting a filter, may be performed.

Correspondingly, the method implemented in the present application may further comprise the following steps:

S1134. Control the brightness of the cast light spot according to a result obtained from the analysis in Step S1131. The analysis result, for example, the features of the image collected in Step S111, comprises a contrast of the image features, a textural feature, and the like.

It should be noted that, a special case of controlling the brightness of the cast light spot is to begin or stop the cast. For example, the cast may be periodically stopped when user keeps gazing at a point. The cast may be stopped when the fundus of the user is bright enough, and the distance from the focusing point of the current sightline of the eye of the user to the eye is detected by using information about the fundus of the user.

In addition, the brightness of the cast light spot may further be controlled according to ambient light.

Preferably, in a method of the embodiment of the present application, Step S113 further comprises:

S1135. Perform calibration on the image of the fundus to obtain at least one reference image corresponding to the image presented by the fundus. Specifically, the collected images and the reference image are compared and calculated to obtain the clearest image. Herein, the clearest image may be an obtained image with a minimum difference from the reference image. In the method of the implementation manner, the difference between the currently obtained image and the reference image is calculated by using an existing image processing algorithm, for example, by using a classical phase difference auto-focus algorithm.

The optical parameter of the eye of the user obtained in Step S1132 may comprise an eye optical axis direction of the user obtained according to the features of the eye of the user when the clearest image is collected. Herein, the features of the eye of the user may be obtained from the clearest image, or may also be obtained elsewhere. The eye optical axis direction of the user represents a gaze direction of the sightline of the eye of the user. Specifically, the eye optical axis direction of the user may be obtained according to the features of the fundus when the clearest image is obtained. The precision of determining the eye optical axis direction of the user by means of the features of the fundus is relatively high.

When a light spot pattern is cast to the fundus, the size of the light spot pattern may be larger or smaller than that of a visible area of the fundus, wherein:

When the area of the light spot pattern is smaller than or equal to that of the visible area of the fundus, a classical feature point matching algorithm (for example, a scale invariant feature transform (SIFT) algorithm) may be used to determine the eye optical axis direction by detecting the position, of the light spot pattern on the image, relative to the fundus.

When the area of the light spot pattern is larger than or equal to the visible area of the fundus, the eye optical axis direction may be determined through the position, of the light spot pattern on the obtained image, relative to an original light spot pattern (obtained by using the image calibration module), so as to further determine the sightline direction of the user.

In another possible implementation manner of the method of the embodiment of the present application, the eye optical axis direction may also be obtained according to features of a pupil of the eye of the user when the clearest image is obtained. Herein, the features of the pupil of the eye of the user may be obtained from the clearest image, or may also be obtained elsewhere. The obtaining an optical axis direction of an eye by means of features of a pupil of an eye of a user is available in the prior art, and is not elaborated herein.

In addition, the method of the embodiment of the present application may further comprise a step of calibrating the eye optical axis direction of the user, so as to determine the eye optical axis direction more precisely.

In the method of the implementation manner, the known imaging parameter comprises a fixed imaging parameter and a real-time imaging parameter, where the real-time imaging parameter is parameter information of the optical device when the clearest image is obtained, and the parameter information may be recorded in real time when the clearest image is obtained.

After the current optical parameter of the eye of the user is obtained, the distance from the eye focusing point of the user to the eye of the user may be obtained through a calculation (specific processes are described in detail in combination with the apparatus part).

In the method of the embodiment of the present application, after the focusing point position of the user is detected in Step S110, Step S120 further comprises:

S121. Obtain a monitoring parameter according to the focusing point position.

According to a different state of the user, the monitoring parameter may comprise one or more of the following: a distance from the focusing point position to the eye of the user, an angle between the current sightline of the user and a specific direction, an angle between the current sightline of the user and a normal which is on a viewed object and passes through the focusing point, and a changing frequency of the focusing point position.

S122. Alert the user according to the monitoring parameter, wherein a manner of the alert may be, for example, making a sound or staring a vibration, changing the color of a light source, making a light source flicker, and the like.

Specifically, a user may be alerted instantly when the monitoring parameter exceeds a preset range. For example, the distance from the focusing point position to the eye of the user exceeds a preset distance range, the angle between the current sightline of the user and a specific direction (for example, a moving direction of the user) exceeds a preset range, the angle between the current sightline of the user and the normal which is on the viewed object and passes through the focusing point exceeds a preset range, the changing frequency of the focusing point position exceeds a preset range, and the like.

A user may also be alerted when a duration the monitoring parameter exceeding a preset range exceeds a preset period of time. That is, when one or more of the foregoing cases where a preset range is exceeded occur, an alert is not sent instantly, and instead is sent after a certain reasonable time range, so as to further improve the precision of the alert.

In the method of the embodiment of the present application, according to a state of the user, one or more monitoring parameters may be selected, and the preset range and the preset period of time are set. Specifically, an eye use scenario of the user can be determined according to a state of the user, and then a proper preset range and a proper preset period of time are set. For example, if it is analyzed by a state of a user that the user is in a reading state, that the distance from the focusing point position to the eye exceeds the preset distance range (to monitor if the user is extremely close to a target reading), that the angle, between the current sightline of the user and the normal which is on the viewed object and passes through the focusing point, exceeds the preset range (to monitor if the posture of the user is extremely inclined), that the changing frequency of the focusing point position exceeds the preset range (to monitor if the user is in a bumpy state that is inappropriate for reading), or the like, may be selected.

The state of the user may comprise a moving state, a health state, a previous eye use history (for example, representing a duration that a reading state or a driving state has lasted, wherein according to the duration, a preset range and a preset period of time of a subsequent alert are adaptively adjusted), and the like, of the user.

During the selection of a monitoring parameter and the setting of a preset range and a preset period of time, user data may also be considered in combination, and the user data may comprise one or more of a vision condition, age, gender, profession, and other information associated with eye use, of a user. The data may be manually input by the user or other people or automatically obtained. As user data is considered in combination, different preset ranges and different preset periods of time may be set for different users in a targeted manner. Correspondingly, the method of the embodiment of the present application further comprises the following steps:

obtaining user data; and setting the preset range and/or the preset period of time according to the user data.

In sum, for the method of the embodiment of the present application, a focusing point position of a sightline of a user can be detected precisely, and the user can be alerted accurately according to the focusing point position, so that the application range of the method is relatively wide. In addition, according to a state of a user, user data, and the like, a monitoring parameter is selected and an alert threshold is set, so that the user can be properly alerted in a more targeted manner.

A person skilled in the art may understand that, in the foregoing method of the specific implementation manners of the present application, serial numbers of the steps do not mean a specific execution sequence, and the execution sequence of each step should be determined according to a function and internal logic of the step, but should not constitute any limitation on an implementation process of specific implementation manners of the present application.

Figure 3:
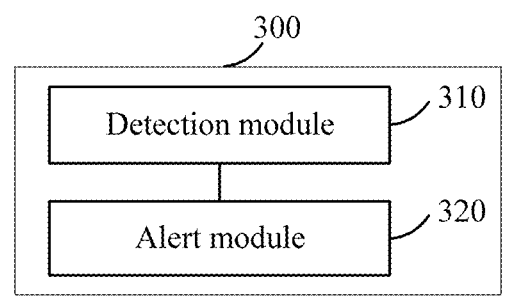
FIG. 3 is an example schematic structural diagram of an alert apparatus according to an embodiment of the present application.

As shown in FIG. 3, an embodiment of the present application further provides an alert apparatus 300. The apparatus 300 comprises:

a detection module 310, configured to detect a focusing point position of a sightline of a user; and an alert module 320, configured to alert the user according to the focusing point position and a state of the user.

For the apparatus of the embodiment of the present application, a focusing point position of a sightline of a user is detected, so as to send an alert more accurately based on an object gazed by the user, so that the application range is relatively wide.

In the apparatus of the embodiment of the present application, the detection module 310 may detect a focusing point position of a sightline of a user in multiple manners. For example:

a) A pupil direction detector is used to detect an eye optical axis direction, and then the depth of filed at which the eye gaze is obtained by using a depth sensor (for example, infrared distance measurement), so that a focusing point position of a sightline of the eye is obtained.

b) Optical axis directions of two eyes are separately detected, and an intersection point of the optical axis directions of the two eyes is obtained, so that a focusing point position of a sightline of an eye is obtained. The technology is also available in the prior art, and is not elaborated herein.

c) According to an optical parameter of an optical path between an image collection device and an eye when a clearest image presented on an imaging surface of the eye is collected, a focusing point position of a sightline of the eye of the user is obtained. In the apparatus of the implementation manner, the detection module 310 may be one of focusing point detection systems shown in FIG. 4(a) to FIG. 4(d), FIG. 5, and FIG. 6.

Figure 4A:
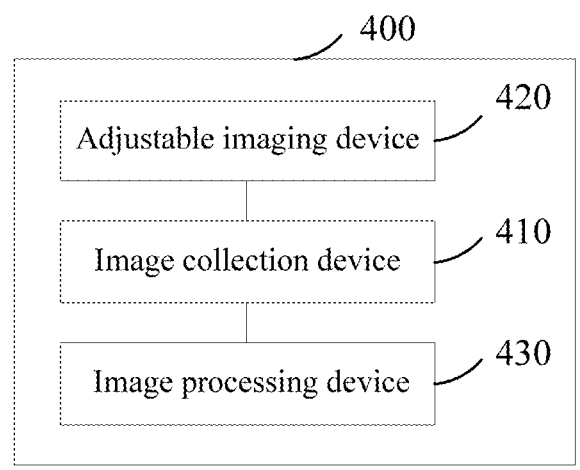
FIG. 4(a) is an example structural block diagram of an eye focusing point detection system of the alert apparatus according to an embodiment of the present application.

As shown in FIG. 4(a), the focusing point detection system 400 comprises:

an image collection device 410, configured to collect an image presented by a fundus of an eye;

an adjustable imaging device 420, configured to adjust an imaging parameter of an optical path between an eye and the image collection device 410, so as to cause the image collection device 410 to obtain a clearest image; and an image processing device 430, configured to process the image obtained by the image collection device 410, and obtain a focusing point position of an eye of a user through calculation according to the imaging parameter of the optical path between the image collection device 410 and the eye of the user when the clearest image is obtained and an optical parameter of the eye.

For the system 400, an image on a fundus of an eye of a user is analyzed and processed to obtain an optical parameter of the eye when a clearest image is obtained by the image collection device, so as to obtain a current focusing point position of the eye of the user through calculation, thereby providing a basis for further alerting the user based on the precise focusing point position.

Figure 4B:
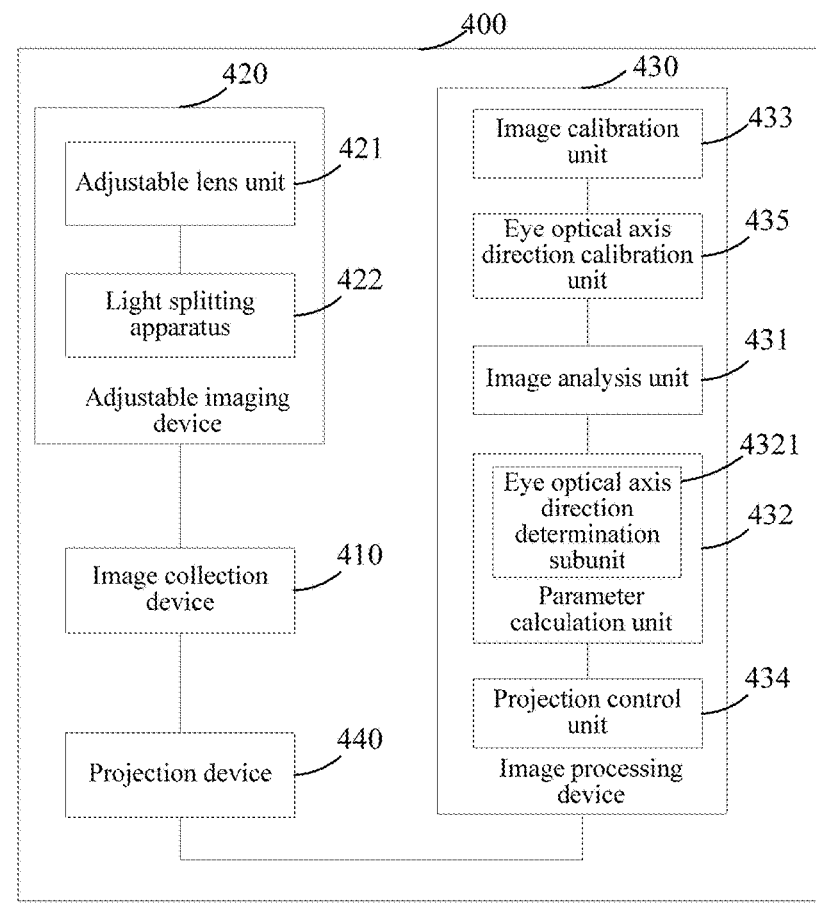
FIG. 4(b) is another example structural block diagram of the eye focusing point detection system of the alert apparatus according to the embodiment of the present application.
Figure 4C:
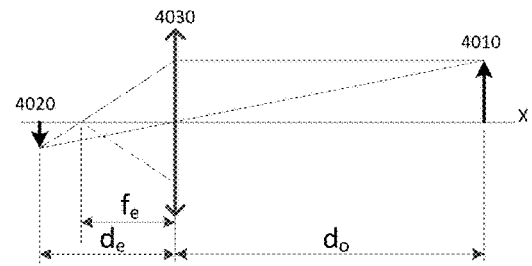
FIG. 4(c) is an example schematic diagram of an imaging optical path of an eye in the eye focusing point detection system of the alert apparatus according to the embodiment of the present application.
Figure 4D:
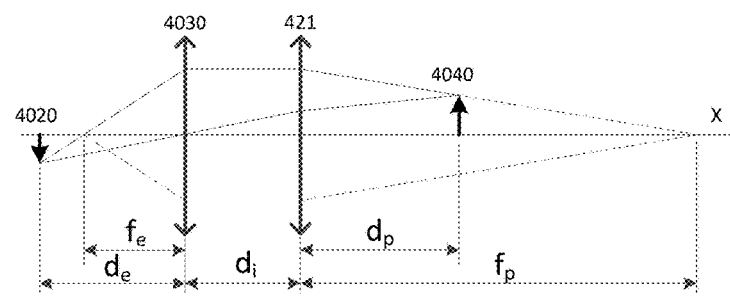
FIG. 4(d) is an example schematic diagram of a distance, from an eye focusing point to an eye, obtained by the eye focusing point detection system of the alert apparatus according to an imaging parameter known to the system and an optical parameter of the eye, according to the embodiment of the present application.

As shown in FIG. 4(b), in a possible implementation manner, the image collection device 410 is a micro camera; in another possible implementation manner of the embodiment of the present application, the image collection device 410 may further use a photosensitive imaging device directly, for example, a charged coupled device (CCD), a complementary metal-oxide semiconductor (CMOS).

As shown in FIG. 4(b), in a possible implementation manner, the adjustable imaging device 420 comprises: an adjustable lens unit 421, located in the optical path between the eye of the user and the image collection device 410, and having an adjustable focal length and/or an adjustable position in the optical path. By using the adjustable lens unit 421, a system equivalent focal length from the eye of the user to the image collection device 410 is adjustable, and by adjusting the adjustable lens unit 421, the image collection device 410 obtains a clearest image of the fundus when the adjustable lens unit 421 is at a certain position or in a certain state. In the implementation manner, the adjustment of the adjustable lens unit 421 in the detection process is continuous and in real time.

In a possible implementation manner, the adjustable lens unit 421 is: a focal length adjustable lens, configured to adjust the refractive index and/or the shape thereof to accomplish the adjustment of the focal length thereof. Specifically: 1) The focal length is adjusted by adjusting the curvature of at least one surface of the focal length adjustable lens; for example, the curvature of the focal length adjustable lens is adjusted by increasing or reducing the liquid medium in a cavity constructed by a double-layer transparent layer. 2) The focal length is adjusted by changing the refractive index of the focal length adjustable lens; for example, the focal length adjustable lens is filled with a specific liquid crystal medium, and the arrangement manner of the liquid crystal medium is adjusted by adjusting a voltage of an electrode corresponding to the liquid crystal medium, so as to change the refractive index of the focal length adjustable lens.

In another possible implementation manner, the adjustable lens unit 421 comprises: a lens set, configured to accomplish the adjustment of the focal length of the lens set by adjusting relative positions between lenses of the lens set.

In addition to the foregoing two methods in which a parameter of an optical path of the system is changed by adjusting features of the adjustable lens unit 421, the parameter of the optical path of the system may also be changed by adjusting the position of the adjustable lens unit 421 in the optical path.

In addition, to avoid affecting experience of a user viewing an viewed object, and to cause the system to be portably applied to a wearable device, the adjustable imaging device 420 further comprises: a light splitting apparatus 422, configured to form light transfer paths between an eye of the user and the viewed object and between the eye of the user and the image collection device 410. Therefore, the optical path may be folded to reduce the volume of the system and to minimize influence on other experience of the user.

The light splitting apparatus 422 may comprise: a first light splitting unit, located between an eye of a user and a viewed object, and configured to transmit light from the viewed object to the eye and transfer the light from the eye of the user to the image collection device 410. The first light splitting unit may be a beam splitter, a light splitting optical waveguide (comprising a fiber) or other proper light splitting devices.

In addition, the image processing device 430 may comprise an optical path calibration unit, configured to perform calibration on the optical path of the system, for example, perform alignment calibration performed on an optical axis of the optical path, and the like, so as to ensure precision of measurement.

An image analysis unit 431 is configured to analyze the images obtained by the image collection device 410 to find the clearest image.

A parameter calculation unit 432 is configured to obtain the optical parameter of the eye of the user through calculation according to the clearest image and the imaging parameter known to the system when the clearest image is obtained.

In the implementation manner, the image collection device 410 may obtain the clearest image by using the adjustable imaging device 420, but the clearest image needs to be found by using the image analysis unit 431. In this case, the optical parameter of the eye may be obtained through calculation according to the clearest image and the parameter, of the optical path, known to the system. Herein, the optical parameter of the eye may comprise an eye optical axis direction of the user.

In a possible implementation manner, the system 400 further comprises: a cast device 440, configured to cast a light spot to the fundus. The function of the cast device 440 may be implemented by using a micro projector. The cast light spot may have no specific pattern and be only configured to light up the fundus. The cast light spot may also comprise a pattern rich in features. The pattern rich in features may facilitate detection, so as to improve the precision of detection. An image, of a fundus, collected when there is a light spot and a light spot pattern are shown in FIG. 2(*a*) and FIG. 2(*b*).

To avoid affecting normal viewing of the eye, preferably, the light spot is an infrared light spot invisible to the eye. In this case, to reduce interferences from other spectrums:

an eye invisible light transmission filter may be disposed on an emergent surface of the cast device 440; and an eye invisible light transmission filter may be disposed on an incident surface of the image collection device 410.

Preferably, in a possible implementation manner, the image processing device 430 further comprises:

a cast control unit 434, configured to control the brightness of the cast light spot of the cast device 440 according to the result obtained by the image analysis unit 431.

For example, the cast control unit 434 may self-adaptively adjust the brightness according to the features of the image obtained by the image collection device 410. Herein, the features of the image comprise a contrast of the image features, a textural feature, and the like.

It should be noted that, a special case of controlling the brightness of the cast light spot by the projection device 440 is to turn on or turn off the cast device 440. For example, the cast device 440 may be periodically turned off when the user keeps gazing at a point. The light source may be turned off when the fundus of the user is bright enough, and the distance from the focusing point of the current sightline of the eye to the eye is detected by using information about the fundus of the user only.

In addition, the cast control unit 434 may further control the brightness of the cast light spot of the cast device 440 according to ambient light.

Preferably, in a possible implementation manner, the image processing device 430 further comprises: an image calibration unit 433, configured to perform calibration on an image of the fundus to obtain at least one reference image corresponding to the image presented by the fundus.

The images obtained by the image collection device 410 and the reference image are compared and calculated by the image analysis unit 431 to obtain the clearest image. Herein, the clearest image may be an obtained image with a minimum difference from the reference image. In the implementation manner, the difference between the currently obtained image and the reference image is calculated by using an existing image processing algorithm, for example, by using a classical phase difference auto-focus algorithm.

Preferably, in a possible implementation manner, the parameter calculation unit 432 comprises:

an eye optical axis direction determination subunit 4321, configured to obtain an eye optical axis direction of a user according to features of the eye of the user when the clearest image is obtained. The features of the eye of the user may be obtained from the clearest image, or may be obtained elsewhere. The eye optical axis direction of the user represents a gaze direction of the eye of the user.

In a possible implementation manner, the eye optical axis direction determination subunit 4321 comprises: a first determination portion, configured to obtain an eye optical axis direction of the user according to features of the fundus when the clearest image is obtained. Compared with obtaining an eye optical axis direction of the user according to features of the pupil and the eyeball surface, the precision of determining an eye optical axis direction of the user according to features of a fundus is higher.

When a light spot pattern is cast to a fundus, the size of the light spot pattern may be larger or smaller than a visible area of the fundus, wherein:

When the area of the light spot pattern is smaller than or equal to the visible area of the fundus, a classical feature point matching algorithm (for example, a SIFT algorithm) may be used to determine the eye optical axis direction by detecting the position, of the light spot pattern on the image, relative to the fundus.

When the area of the light spot pattern is larger than or equal to the visible area of the fundus, the eye optical axis direction may be determined by the position, of the light spot pattern on the obtained image, relative to an original light spot pattern (obtained by using the image calibration module), so as to further determine the sightline direction of the user.

In another implementation manner, the eye optical axis direction determination subunit 4321 comprises: a second determination portion, configured to obtain the eye optical axis direction of the user according to features of the pupil of the eye of the user when the clearest image is obtained. Herein, the features of the pupil of the eye of the user may be obtained from the clearest image, or may be obtained elsewhere. The obtaining an eye optical axis direction of the user according to features of a pupil of an eye of a user is available in the prior art, and is not elaborated herein.

In a possible implementation manner, the image processing device 430 further comprises: an eye optical axis direction calibration unit 435, configured to perform calibration on the eye optical axis direction of the user, so as to determine the eye optical axis direction of the user more precisely.

In the implementation manner, the imaging parameter known to the system comprises a fixed imaging parameter and a real-time imaging parameter, wherein the real-time imaging parameter is parameter information of the adjustable lens unit when the clearest image is obtained, and the parameter information may be recorded in real time when the clearest image is obtained.

After the current optical parameter of the eye of the user is obtained, the distance from the eye focusing point to the eye may be obtained through calculation, specifically:

FIG. 4(*c*) is a schematic diagram of eye imaging, and in combination with a lens imaging formula in a classical optics theory, formula (1) may be obtained from FIG. 4(*c*):

$$\frac{1}{d_o} + \frac{1}{d_e} = \frac{1}{f_e} \qquad (1)$$

where $d_o$ and $d_e$ represent distances from a current viewed object 4010 and a real image 4020 on the retina to an eye equivalent lens 4030 respectively, $f_e$ represents an equivalent focal length of the eye equivalent lens 4030, and X represents an the eye optical axis direction (that is, an optical axis of a sightline).

FIG. 4(*d*) is a schematic diagram of a distance, from the eye focusing point to the eye, obtained according to an optical parameter known to the system and an optical parameter of the eye. In FIG. 4(*d*), a light spot 4040 forms a virtual image (not shown) through the adjustable lens unit 421, and suppose that the distance from the virtual image to the adjustable lens unit 421 is x, the following system of equations may be obtained in combination with the formula (1):

$$\begin{cases} \dfrac{1}{d_p} - \dfrac{1}{x} = \dfrac{1}{f_p} \\ \dfrac{1}{d_i + x} + \dfrac{1}{d_e} = \dfrac{1}{f_e} \end{cases} \qquad (2)$$

$d_p$ represents an optical equivalent distance from the light spot 4040 to the adjustable lens unit 421, $d_i$ represents an optical equivalent distance from the adjustable lens unit 421 to the eye equivalent lens 4030, $f_p$ represents a focal length value of the adjustable lens unit 421, and $d_i$ represents is a distance from the eye equivalent lens 4030 to the adjustable lens unit 421.

It can be obtained from (1) and (2) that the distance from the current viewed object 4010 (eye focusing point) to the eye equivalent lens 4030 is shown in formula (3):

$$d_o = d_i + \frac{d_p \cdot f_p}{f_p - d_p} \qquad (3)$$

According to the distance from the viewed object 4010 to the eye obtained through calculation, and the eye optical axis direction that may be obtained from the previous record, the focusing point position of the eye may be easily obtained.

Figure 5:
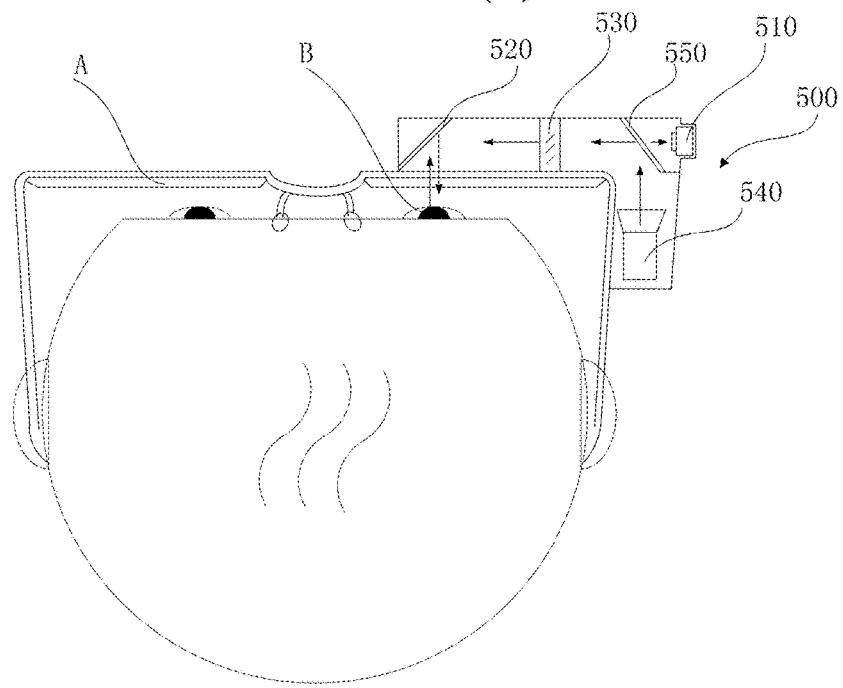
FIG. 5 is an example schematic diagram of the eye focusing point detection system, of the alert apparatus, applied to a pair of glasses, according to an embodiment of the present application.

FIG. 5 shows an embodiment in which an eye focusing point detection system 500 of a possible implementation manner is applied to glasses A (here, the glasses A may be an alert apparatus of the embodiment of the present application), and comprises content recorded in the implementation manner shown in FIG. 4(*b*); specifically: as can be seen from FIG. 5, in the implementation manner, the system 500 of the implementation manner is integrated on the right side (not limited herein) of the glasses A, and comprises:

a micro camera 510, whose function is the same as that of the image collection device recorded in the implementation manner shown in FIG. 4(*b*), and disposed on the right exterior side of an eye B to avoid affecting a sightline of a user in viewing an object;

a first beam splitter 520, whose function is the same as that of the first light splitting unit recorded in the implementation manner shown in FIG. 4(*b*), and disposed at an intersection point of a gaze direction of the eye B and an incident direction of the camera 510 at a certain slant angle to transmit light that is from the viewed object entering the eye B and reflect light that is from the eye to the camera 510; and a focal length adjustable lens 530, whose function is the same as that of the focal length adjustable lens recorded in the implementation manner shown in FIG. 4(*b*), and located between the first beam splitter 520 and the camera 510 to adjust a focal length value in real time, so as to cause the camera 510 to photograph a clearest image of the fundus at a certain focal length value.

In the implementation manner, the image processing device is not shown in FIG. 5, and the function of the image processing device is the same as that of the image processing device shown in FIG. 4(*b*).

Since the brightness of the fundus is usually insufficient, it is recommended to light up the fundus, and in the implementation manner, a light source 540 is used to light up the fundus. To avoid affecting experience of the user, herein, preferably, the light source 540 is eye invisible light, and preferably is a near-infrared light source which has little influence on the eye B and to which the camera 510 is sensitive.

In the implementation manner, the light source 540 is located on the outside of a right spectacle frame, so that the transfer of light sent by the light source 540 to the fundus needs to be accomplished by a second beam splitter 550 and the first beam splitter 520 together. In the implementation manner, the second beam splitter 550 is also located in front of an incident surface of the camera 510, so that light from the fundus to the second beam splitter 550 needs to be transmitted.

It can be seen that, in the implementation manner, to improve the user experience and the collection resolution of the camera 510, the first beam splitter 520 preferably may have features of high infrared reflectance and high visible light transmittance. For example, an infrared reflective film may be disposed on a side, towards the eye B, of the first beam splitter 520, so as to implement the foregoing features.

As can be seen from FIG. 5, because in the implementation manner, the eye focusing point detection system 500 is located on a side, away from the eye B, of a lens of the glasses A, during calculation of the eye optical parameter, the lens can be regarded as a part of the glasses, and the optical features of the lenses do not need to be known.

In another implementation manner of the embodiment of the present application, the eye focusing point detection system 500 may be located on a side, close to the eye B, of the lens of the glasses A. In this case, a parameter of the optical feature of the lens needs to be obtained in advance, and influence factors of the lens are taken into consideration during calculation of the focusing point distance.

The light sent by the light source is reflected by the second beam splitter 550, cast by the focal length adjustable lens 530, and reflected by the first beam splitter 520, then enters the eye of the user through the lens of the glasses A, and finally reaches the retina of the fundus. The camera 510 photographs the image of the fundus through the pupil of the eye B via the optical path constructed by the first beam splitter 520, the focal length adjustable lens 530, and the second beam splitter 550.

Figure 6:
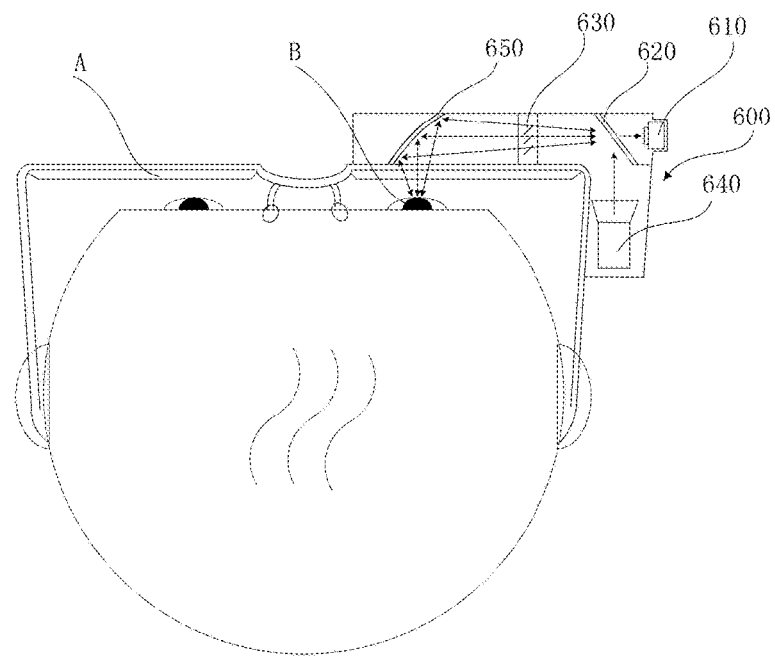
FIG. 6 is an example schematic diagram of the eye focusing point detection system, of the alert apparatus, applied to a pair of glasses, according to an embodiment of the present application.

FIG. 6 is a schematic structural diagram of an eye focusing point detection system 600 in another implementation manner. As can be seen from FIG. 6, the implementation manner is similar to the implementation manner shown in FIG. 5, comprising a micro camera 610, a second beam splitter 620, and a focal length adjustable lens 630. The differences are that a cast apparatus 640 in the implementation manner is the cast apparatus 640 for casting a light spot pattern, and that a curved beam splitter 650 is used as a curved light splitting unit to replace the first beam splitter in the implementation manner shown in FIG. 5.

Herein, the curved beam splitter 650 is used to transfer, to the image collection device, images presented by the fundus and separately corresponding to positions of a pupil in the case of different eye optical axis directions. Therefore, the camera may photograph an image mixed and superimposed of all angles of the eyeball; however, because only the part of the fundus through the pupil can achieve clear imaging on the camera, and other parts fail to be clearly imaged due to out of focus, so that no severe interference is caused on the imaging of the fundus and the feature of the fundus can still be detected. Therefore, compared with the implementation manner shown in FIG. 5, in the implementation manner, the image of the fundus can be desirably obtained when an eye gazes in different directions, making the eye focusing point detection system of the implementation manner have a relatively wide application range and relatively high precision of detection.

Figure 7:
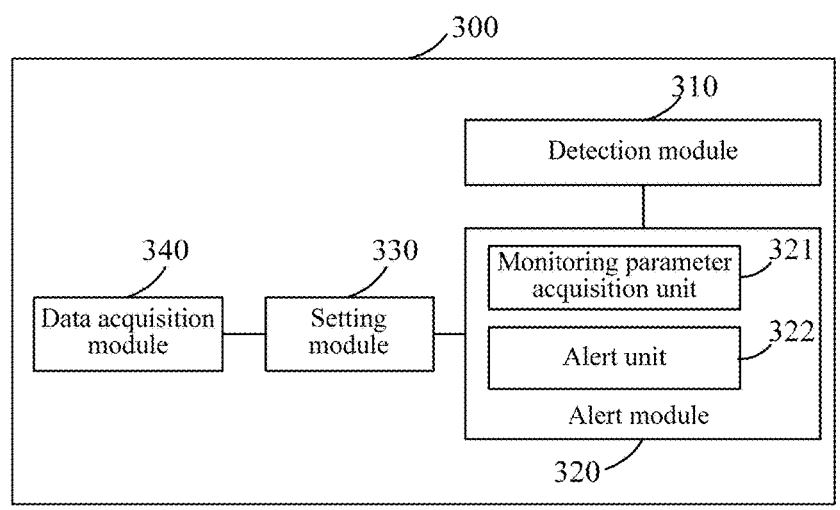
FIG. 7 is another example schematic structural diagram of the alert apparatus according to an embodiment of the present application.

As shown in FIG. 7, in the alert apparatus 300 of the embodiment of the present application, the alert module 320 further comprises a monitoring parameter obtaining unit 321 and an alert unit 322.

The monitoring parameter obtaining unit 321 is configured to obtain a monitoring parameter according to the focusing point position.

According to a different state of a user, the monitoring parameter may comprise one or more of the following: a distance from the focusing point position to an eye of the user, an angle between a current sightline of the user and a specific direction, an angle between a current sightline of the user and a normal which is on a viewed object and passes through the focusing point, and a changing frequency of the focusing point position.

The alert unit 322 is configured to alert the user according to the monitoring parameter, wherein a manner of the alert is, for example, making a sound or staring a vibration, changing the color of a light source, making a light source flicker, and the like.

Specifically, a user may be alerted instantly when the monitoring parameter exceeds a preset range. For example, the distance from the focusing point position to the eye of the user exceeds a preset distance range, the angle between the current sightline of the user and a specific direction (for example, a moving direction of the user) exceeds a preset range, the angle between the current sightline of the user and the normal which is on a viewed object and passes through the focusing point exceeds a preset range, the changing frequency of the focusing point position exceeds a preset range, and the like.

A user may also be alerted when a duration monitoring parameter exceeding a preset range exceeds a preset period of time. That is, when the foregoing cases where a preset range is exceeded occur, an alert is not sent instantly, and instead is sent after a certain reasonable time range, so as to further improve the precision of the alert.

The alert unit 322 may comprise an alert device and a timing device having the foregoing functions correspondingly, which is not elaborated herein.

In addition, the apparatus 300 of the embodiment of the present application may further comprise a setting module 330, configured to set the preset range and the preset period of time. The setting module 330 may select one or more monitoring parameters according to a state of the user, and set the preset range and the preset period of time. Specifically, an eye use scenario of the user can be determined according to a state of the user, and then a proper preset range and a proper preset period of time are set. For example, if it is analyzed by a state of a user that the user is in a reading state, that the distance from the focusing point position to the eye exceeds a preset distance range (to monitor if the user is extremely close to a target reading), that the angle, between the current sightline of the user and the normal which is on the viewed object and passes through the focusing point, exceeds a preset range (to monitor if the posture of the user is extremely inclined), that the changing frequency of the focusing point position exceeds a preset range (to monitor if the user is in a bumpy state that is inappropriate for reading), or the like, may be selected.

The state of the user may comprise a moving state, a health state, a previous eye use history (for example, representing a duration that a reading state has lasted, wherein according to the duration, a preset range and a preset period of time of a subsequent alert are adaptively adjusted), and the like, of the user. The detection of a state of the user may be accomplished by the detection module 310, and according to the detected different state of the user, the detection module 310 may further be formed of different components; for example, for a moving state, the detection module 310 may further comprise a Global Positioning System (GPS) positioning device and a head sensor, so as to detect the moving state of the user according to positioning information and/or head sensing information.

During the selection of a monitoring parameter and the setting of a preset range and a preset period of time, the setting module 330 may consider user data in combination, and the user data may comprise one or more of a vision condition, age, gender, profession, and other information associated with eye use, of a user. The data may be manually input by the user or other people or automatically obtained. As user data is considered in combination, different preset ranges and different preset periods of time may be set for different users in a targeted manner. Correspondingly, the apparatus 300 of the embodiment of the present application further comprises: a data obtaining module 340, configured to obtain user data.

The method and apparatus of the embodiments of the present application are further described below by using specific examples.

Figure 8:
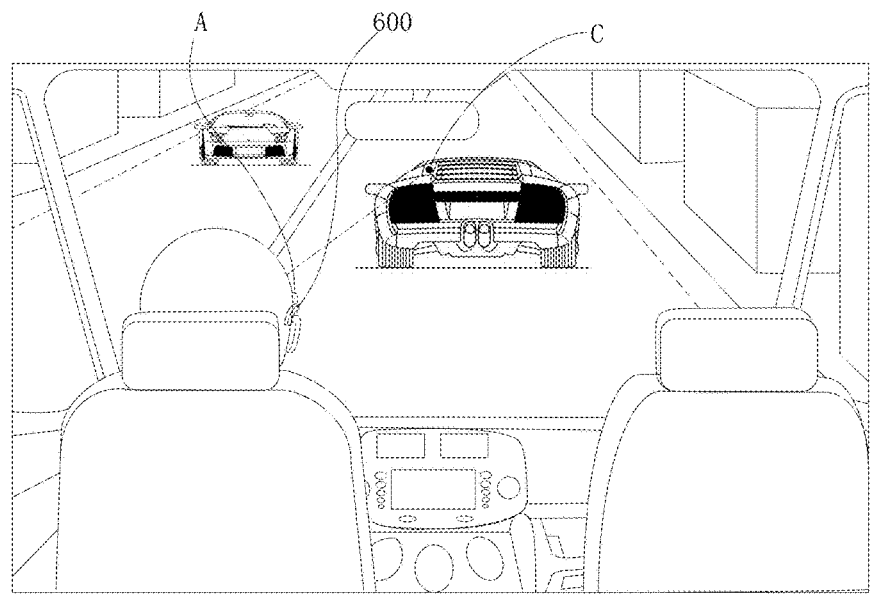
FIG. 8 is an example schematic diagram of the apparatus being used in a driving state according to an embodiment of the present application.

A driving scenario shown in FIG. 8 is used as an example. A driver wears an alert apparatus (the glasses A) according to a possible implementation manner of an embodiment of the present application, the focusing point detection system 600 shown in FIG. 6 is assembled on the alert apparatus, a timing device is disposed in the alert apparatus of this example, and the timing device may separately record varied time periods associated with a state of a user.

In this scenario, the process of using the alert apparatus to alert the user is as follows:

A state of the user is detected. It is determined that the user is in a moving state according to GPS positioning information, and preset ranges suitable for safe driving are set: 1) a threshold S1 of a safe distance from a target object in front; 2) a safe range R1 of an included angle between a sightline of the user and a travel direction and a first time threshold T1 (for example, 10 seconds); and 3) a second time threshold T2 (for example, 1 hour) for resetting the thresholds and the range set in 1) and 2). According to detection of a focusing point position, it is determined that, when a distance from a focusing point C to the eye of the user is shorter than the distance threshold S1, the user is alerted in a vibration manner to avoid affecting driving. When the included angle between the sightline of the user and the travel direction exceeds the safe range R1 and the duration exceeds the second time threshold T1, the user is alerted likewise.

When the total driving duration of the user exceeds 1 hour, the alert apparatus automatically resets the thresholds and the range set in 1) and 2), and to ensure driving safety, S1, R1, and T2 may be reduced or shortened correspondingly.

It should be noted that, if it is determined according to GPS positioning information that the user is in a static state (for example, waiting at a red light), the alert function of the alert apparatus may be stopped, and be restarted when the alert apparatus is restarted.

Figure 9:
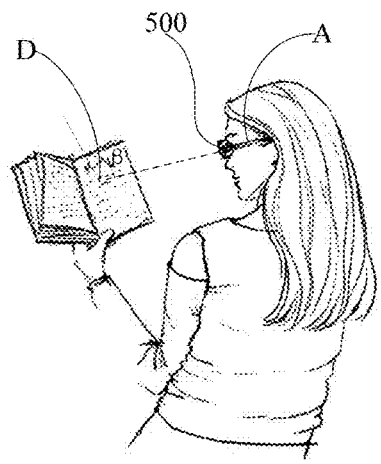
FIG. 9 is an example schematic diagram of the apparatus being used in a reading state according to an embodiment of the present application.

A reading scenario shown in FIG. 9 is used as an example. A user wears an alert apparatus (the glasses A) according to a possible implementation manner of an embodiment of the present application, the focusing point detection system 500 shown in FIG. 5 is assembled on the alert apparatus, a timing device is disposed in the alert apparatus of this embodiment, and the timing device may separately record varied time periods associated with a state of the user.

In this scenario, the process of using the alert apparatus to alert the user is as follows:

Preset ranges suitable for vision protection are set: 1) a threshold S2 of a safe distance from a target object in front; 2) a range R2 of an included angle β between a current sightline of the user and a normal which is on a viewed object and passes through the focusing point D, and a third time threshold T3 (for example, 1 minute); 3) a changing frequency F1 of the focusing point position, and a fourth time threshold T4 (for example, 5 minutes); and 4) a fifth time threshold T5 (for example, 1 hour) for resetting the foregoing thresholds and range.

According to detection of the focusing point position, when a distance between the focusing point D and the eye of the user is shorter than S2, the user is alerted in a voice manner. When the included angle β exceeds the range R2, and the duration exceeds T3, the user is alerted. When a changing frequency of the focusing point position exceeds F1 and the duration exceeds T4, the user may be in a quick moving state at this time, and the user is alerted to stop reading.

When a total reading duration of the user exceeds T5, the alert apparatus automatically resets the foregoing thresholds and range and makes proper reduction or shortening.

Figure 10:
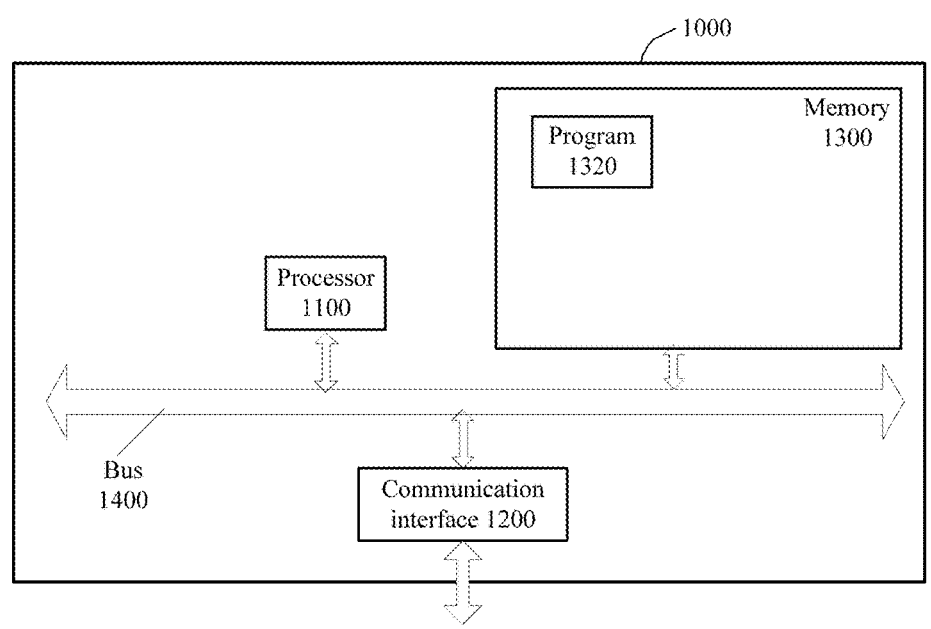
FIG. 10 is yet another example schematic structural diagram of the alert apparatus according to an embodiment of the present application.

FIG. 10 is a schematic structural diagram of an alert apparatus 1000 provided in an embodiment of the present application, and a specific implementation of the alert apparatus 1000 is not limited by the specific embodiment of the present application. As shown in FIG. 10, the alert apparatus 1000 may comprise:

a processor 1100, a communications interface 1200, a memory 1300, and a communication bus 1400. Wherein:

Communication among the processor 1100, the communications interface 1200, and the memory 1300 is accomplished through the communication bus 1400.

The communications interface 1200 is configured to communicate with a network element such as a client.

The processor 1100 is configured to execute a program 1320, and specifically associated steps in the method embodiment shown in FIG. 1 may be executed.

Specifically, the program 1320 may comprise a program code, wherein the program code comprises a computer operation instruction.

The processor 1100 may be a central processing unit (CPU), an application specific integrated circuit (ASIC) or one or more integrated circuits configured to implement the embodiment of the present application.

The memory 1300 is configured to store the program 1320. The memory 1300 may comprise a high-speed random access memory (RAM), and may also comprise a nonvolatile memory, for example, at least one disk memory. The program 1320 specifically can cause the apparatus 1000 to execute the following steps:

Detect a focusing point position of a sightline of a user.

Alert the user according to the focusing point position and a state of the user.

For a specific implementation of each unit in the program 1320, reference may be made to a corresponding step or unit in each embodiment of the foregoing text, which is not elaborated herein.

An embodiment of the present application further provides a wearable optical device, wherein the wearable optical device may be a pair of frame glasses shown in FIG. 5 or FIG. 6, or may be contact lenses, and the wearable optical device comprises the alert apparatus recorded in each of the foregoing embodiments.

In another possible implementation manner of the embodiment of the present application, the eye optical parameter detection system may also be applied to other devices associated to eyes, for example, a non-wearable optical device such as a telescope; or, the optical parameter detection system of the present application may also be applied to other imaging and receiving apparatuses such as a camera apart from eyes.

A person of ordinary skill in the art may be aware that, the exemplary units and method steps described in the embodiments disclosed herein may be implemented by electronic hardware or a combination of computer software and electronic hardware. Whether the functions are performed in the form of hardware or software depends on particular applications and design constraint conditions of the technical solutions. A person skilled in the art may use different methods to implement the described functions for each particular application, but it should not be considered that the implementation goes beyond the scope of the present invention.

When the functions are implemented in a form of a software functional unit, and are sold or used as an independent product, the functions may be stored in a computer-readable storage medium. Based on such an understanding, the technical solutions of the present application essentially, or the part contributing to the prior art, or a part of the technical solutions may be implemented in a form of a software product. The computer software product is stored in a storage medium and comprises several instructions for instructing a computer device (which may be a personal computer, a server, a network device or the like) to perform all or a part of the steps of the method described in the embodiment of the present application. The foregoing storage medium comprises any medium that can store program code, such as a USB flash drive, a removable hard disk, a read-only memory (ROM), a RAM, a magnetic disk or an optical disc.

The foregoing implementation manners are only used for describing the present application, and are not intended to limit the present application. A person of ordinary skill in the art may make various changes and variations without departing from the spirit and scope of the present application; therefore, any equivalent technical solution falls within the scope of the present application, and patent protection scope of the present application shall be defined by claims.

What is claimed is:

1. A method performed by a system comprising a processor, comprising:

casting a light spot having a pattern to a fundus of an eye of a user;

collecting at least one image comprising a patterned image, corresponding to the pattern, as presented by the fundus;

adjusting a first focal length of an adjustable lens on an optical path between the eye of the user and an image collection device, and a first distance from an equivalent lens for the eye to the adjustable lens to collect a clearest image of the patterned image corresponding to the pattern and presented by the fundus, wherein the light spot forms a virtual image through the adjustable lens;

in response to the clearest image being collected, determining a focusing point position according to the first focal length of the adjustable lens, the first distance from the equivalent lens to the adjustable lens, a second focal length of the equivalent lens, a second distance between the patterned image presented by the fundus and the equivalent lens, an optical distance between the light spot and the adjustable lens, and a third distance between the virtual image and the adjustable lens; and obtaining at least one monitoring parameter according to the focusing point position, the at least one monitoring parameter comprising at least one of:

a first angle between a current sightline of the user and a specific direction, or a second angle between the current sightline of the user and a normal which is on a viewed object and passes through the focusing point position.

2. The method of claim 1, wherein an eye optical axis direction of the user is also used to determine the focusing point position.

3. The method of claim 1, further comprising:

transferring, respectively, an image of the at least one image of the patterned image, corresponding to the pattern, as presented by the fundus to the collecting position according to positions of a pupil associated with different eye optical axis directions.

4. The method of claim 1, further comprising:

detecting a state of the user.

5. The method of claim 1, further comprising generating an alert, wherein the generating the alert comprises:

generating the alert for the user in response to the at least one monitoring parameter being determined to exceed a preset range.

6. The method of claim 1, further comprising generating an alert, wherein the generating the alert comprises:

generating the alert for the user in response to a duration of the at least one monitoring parameter being determined to exceed a preset range for a preset period of time.

7. The method of claim 1, wherein the specific direction is a moving direction of the user.

8. The method of claim 5, further comprising:

setting the preset range according to a state of the user.

9. The method of claim 6, further comprising:

setting the preset period of time according to a state of the user.

10. The method of claim 5, further comprising:

obtaining user data; and setting the preset range according to the user data.

11. The method of claim 6, further comprising:

obtaining user data; and setting the preset period of time according to the user data.

12. An apparatus, comprising:

a memory that stores executable modules; and a processor, coupled to the memory, that executes the executable modules to perform operations of the apparatus, the executable modules comprising:
   a detection module configured to detect a focusing point position of a current sightline of a user, wherein the detection module is communicatively coupled to:
     a casting device configured to cast a light spot having a pattern to a fundus of an eye of the user;
     an image collection device configured to collect at least one image comprising a patterned image representing the pattern as presented by the fundus of the eye of the user;
     an adjustable imaging device configured to adjust a first focal length of an adjustable lens on an optical path between the eye of the user and the image collection device, and a first distance from an equivalent lens for the eye to the adjustable lens, wherein the image collection device collects a clearest image of the patterned image and the light spot forms a virtual image through the adjustable lens; and
     an image processing device configured to obtain, in response to the clearest image being collected, a focusing point position through calculation according to the first focal length of the adjustable lens, the first distance from the equivalent lens to the adjustable lens, a second focal length of the equivalent lens, a second distance between the patterned image presented by the fundus and the equivalent lens, an optical distance between the light spot and the adjustable lens, and a third distance between the virtual image and the adjustable lens; and
   an alert module configured to obtain at least one monitoring parameter according to the focusing point position, the at least one monitoring parameter comprising at least one of:
     a first angle between the current sightline of the user and a specified direction, or
     a second angle between the current sightline of the user and a normal which is on a viewed object and passes through the focusing point position, and alert the user according to the at least one monitoring parameter and a state of the user.

13. The apparatus of claim 12, wherein the adjustable imaging device further comprises:
a curved light splitting unit configured to, respectively, transfer an image of the at least one patterned image presented by the fundus of the eye of the user to the image collection device according to positions of a pupil associated with different eye optical axis directions.

14. The apparatus of claim 12, wherein the detection module is further configured to detect the state of the user.

15. The apparatus of claim 12, wherein an alert unit generates an alert for the user in response to the at least one monitoring parameter being determined to exceed a preset range.

16. The apparatus of claim 12, wherein an alert unit generates an alert for the user in response to a duration of the at least one monitoring parameter exceeding a preset range being determined to exceed a preset period of time.

17. The apparatus of claim 15, further comprising:
a setting module configured to set the preset range according to the state of the user.

18. The apparatus of claim 17, further comprising:
a setting module configured to set the preset period of time according to the state of the user.

19. The apparatus of claim 15, further comprising:
a data obtaining module configured to obtain user data; and
a setting module configured to set the preset range according to the user data.

20. The apparatus of claim 16, further comprising:
a data obtaining module configured to obtain user data; and
a setting module configured to set the preset period of time according to the user data.

21. The apparatus of claim 12, wherein the apparatus is a pair of glasses.

22. A computer readable storage device comprising executable instructions that, in response to execution, cause a system comprising a processor to perform operations, comprising:
   determining a focusing point position of a current sightline determined for at least one eye of a user, wherein the focusing point position is determined by:
     casting a light spot having a pattern to a fundus of the user;
     collecting at least one image comprising a representation of the pattern as presented by the fundus of the user;
     adjusting a first focal length of an adjustable lens on an optical path between an eye of the at least one eye of the user and an image collection device, and a first distance from an equivalent lens for the eye to the adjustable lens to collect a clearest image of the at least one image, wherein the clearest image corresponds to a clearest representation of the pattern as presented by the fundus of the user, and wherein the light spot forms a virtual image through the adjustable lens;
   obtaining at least one monitoring parameter according to the focusing point position, the monitoring parameter comprising at least one of:
     a first angle between the current sightline of the user and a specific direction, or
     a second angle between the current sightline of the user and a normal which is on a viewed object and passes through the focusing point position, and
   computing, in response to the clearest image being collected, the focusing point position based on the first focal length of the adjustable lens, the first distance from the equivalent lens to the adjustable lens, a second focal length of the equivalent lens, a second distance between the pattern presented by the fundus and the equivalent lens, an optical distance between the light spot and the adjustable lens, and a third distance between the virtual image and the adjustable lens; and
   outputting an alert to the user according to the at least one monitoring parameter and a state of the user.

23. The computer readable storage device of claim 22, wherein the focusing point position is further determined by:
an eye optical axis direction of the user.

24. The computer readable storage device of claim 22, the operations further comprising:
transferring an image of the at least one image of the pattern, corresponding to the pattern presented by the fundus, to the collecting position according to positions of a pupil associated with different eye optical axis directions.

25. The computer readable storage device of claim 22, the operations further comprising:
  detecting the state of the user.

26. An apparatus, comprising:
  a first device for determining a focusing point position of a current sightline of an eye of a user, wherein, the focusing point position is determined by:
    casting a light spot having a pattern to a fundus of the user;
    collecting at least one image comprising a representation of the pattern as presented by the fundus of the user;
    adjusting a first focal length of an adjustable lens on an optical path between an eye of the at least one eye of the user and an image collection device, and a first distance from an equivalent lens for the eye to the adjustable lens to collect a clearest image of the at least one image, wherein the clearest image corresponds to a clearest representation of the pattern as presented by the fundus of the user, and the light spot forms a virtual image through the adjustable lens;
    computing, in response to the clearest image being collected, a focusing point position based on the first focal length of the adjustable lens, the first distance from the equivalent lens to the adjustable lens, a second focal length of the equivalent lens, a second distance between the pattern as presented by the fundus and the equivalent lens, an optical distance between the light spot and the adjustable lens, and a third distance between the virtual image and the adjustable lens, and
    obtaining at least one monitoring parameter according to the focusing point position, the monitoring parameter comprising at least one of:
      a first angle between the current sightline of the user and a specified direction, or
      a second angle between the current sightline of the user and a normal which is on a viewed object and passes through the focusing point position; and
  a second device for outputting an alert to the user according to the at least one monitoring parameter, the focusing point position, and a state of the user.

27. The apparatus of claim 26, wherein an eye optical axis direction of the user is used to determine the focusing point position.

28. The apparatus of claim 26, wherein an image of the at least one image comprising the representation of the pattern is transferred to the image collection device according to positions of a pupil associated with different eye optical axis directions.

* * * * *